(12) United States Patent
Weng et al.

(10) Patent No.: US 7,353,058 B2
(45) Date of Patent: Apr. 1, 2008

(54) BIO-IMPEDANCE SENSING DEVICE FOR HOMECARE AND EHEALTH

(75) Inventors: Ching Sung Weng, Jhongli (TW); Wei Chih Hu, Jhongli (TW); Cheng I Yang, Hsing-Dieng (TW); Hsien Chung Chen, HsinChu (TW); Fei Wen Huang, Jhongli (TW)

(73) Assignee: Healthy Biotech Corp. Ltd., Banciao, Taipei County (TW)

( * ) Notice: Subject to any disclaimer, the term of this patent is extended or adjusted under 35 U.S.C. 154(b) by 97 days.

(21) Appl. No.: 11/295,583

(22) Filed: Dec. 7, 2005

(65) Prior Publication Data
US 2007/0159372 A1    Jul. 12, 2007

(51) Int. Cl.
*A61B 5/05* (2006.01)

(52) U.S. Cl. .................. 600/547; 600/546

(58) Field of Classification Search .......... 600/547
See application file for complete search history.

(56) References Cited
U.S. PATENT DOCUMENTS

| | | | | |
|---|---|---|---|---|
| 4,155,351 A | * | 5/1979 | Teshima et al. | 600/547 |
| 4,694,840 A | * | 9/1987 | Kairis et al. | 600/548 |
| 5,012,816 A | * | 5/1991 | Lederer | 600/548 |
| 5,961,471 A | * | 10/1999 | Nickson | 600/546 |
| 6,337,994 B1 | * | 1/2002 | Stoianovici et al. | 600/547 |
| 6,360,124 B1 | * | 3/2002 | Iwabuchi | 600/547 |
| 6,823,212 B2 | * | 11/2004 | Pinyayev | 600/547 |
| 6,847,841 B1 | * | 1/2005 | El Hatw | 600/547 |
| 6,993,383 B2 | * | 1/2006 | Assenheimer | 600/547 |
| 7,082,325 B2 | * | 7/2006 | Hashimshony et al. | 600/411 |
| 7,161,364 B1 | * | 1/2007 | Nickson | 324/754 |

* cited by examiner

*Primary Examiner*—Khai M. Nguyen

(57) ABSTRACT

The impedance measuring device of the present invention is a self-operated pressure point impedance measuring device. The device can quantitatively measure the impedance of the pressure point in digital format. The qualified impedance data can be on-line interface to a PC computer for recording and further application using USB protocol. The configuration of device includes a hand-held body or with a parallel connected unit as a current loop; a flexible round point as a measuring point, and an impedance sensing circuitry. This impedance measuring device of the present invention can significantly provide convenience to the users for measuring the impedance.

9 Claims, 7 Drawing Sheets

BIO-IMPEDANCE SENSING DEVICE FOR HOMECARE AND EHEALTH

BACKGROUND OF THE INVENTION (a) Field of the Invention

This invention is related to the electrical impedance measurement of biological body, in particular, an on-line and self-operated electrical impedance measurement of biological body.

(b) Description of the Prior Art

The impedance measurement is based on the theory of Chinese tradition medicine that states that the vitality of internal organ would reflect to some pressure points on human body. In other words, the status of specific group pressure points can be used to diagnose diseases in theory. The physiological status of pressure point includes itching, sour, pain and many others. The physical status of the pressure point on the skin is related to the electrical conduction. Dr. Croon first announced the discovery of low electrical impedance in relationship to the pressure point area in 1947. Subsequently Dr. Yoshio Nakatani further established that the impedance measured of a certain pressure points group were related to specific disease in human. The connection of the group of pressure point that had good electrical conduction was named as Ryodorku. This innovation is based on this prior knowledge to devise an easy operating apparatus for impedance measurement.

SUMMARY OF THE INVENTION

The object of this invention is to provide a simple apparatus that can easily operated (self-operated in particular) for impedance measurement in homecare and e-Health environment. The measurement of impedance can be completed in one step operating procedure. The one button instrument when pressed will activate the impedance sensing and detection circuit. A LED light cooperated with a beeping sound will be indicate the completion of the impedance measurement. The acquired data, the value of impedance of the measuring area, will be transmitted to PC on line through USB communication protocol.

In order to achieve such novelty, four unique designs have been made to accomplish such object. (1) The contact of the probe (12) applied to the measuring object, the pressure applied to the surface of measuring object, should be consistent. (2) The proper pressure applied to the probe (12) will activate the impedance measurement mechanism. (3) When the data acquisition is successfully completed, the user will be notified by the beeping sound and LED light indicator. And, (4) the device can be self-operate or, with an extra electrical lead, a helping personnel can operate the device.

The innovated device, the electrical impedance measuring device for homecare and e-Health environment, has a shape of a pen with a hallow interior so that it can be hand held by the user. The hand held portion is consisted of one electrical lead of the device. The other electrical lead of the device, the electrical probe (12), is located at the front end of the device. The probe (12) is connected to an elastic unit for absorbing impact pressure and for applying proper pressure. The hallow interior of the device comprises an impedance measuring circuitry (20). The functional blocks of impedance measuring circuitry (20) includes (1) a power management unit that provides proper isolated DC power to the circuitry; (2) a function generator; (3) a microprocessor controlled functional unit for the signal digitization, the USB data communication, and the control of the signal processing flow; and (4) a user interface button to activate the function of microprocessor.

The preferred USB communication interface of the electrical impedance measuring device for homecare and e-Health environment is positioned at the rear end of the device that can be connected to a personal computer. The USB connection is used for data communication and will be able to receive power from computer. The received power will be converted to proper voltage level that will be providing isolated power to the circuitry. There is an extra electrical lead connected in parallel with hand held body and positioned at the rear end of the device as USB connection.

The electrical impedance measuring device of the present invention is a self-operated instrument. With an extra electrical lead, the device can be used for measuring subject's impedance with help of others. The electrical impedance measuring device can be connected to a personal computer through the USB connection. The required power to operate the circuitry is delivered from computer and the advantage of USB connection. The power management unit of the device will isolate the power usage of device from the power source.

DETAILED DESCRIPTION OF THE PREFERRED EMBODIMENT

Figure 1:
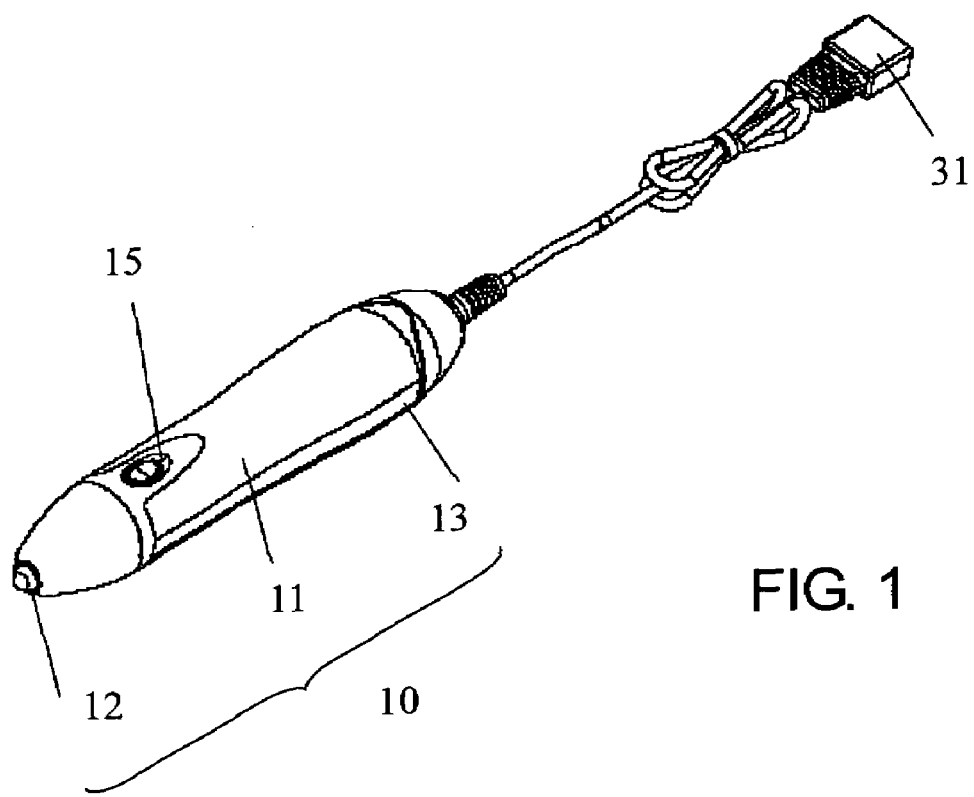
FIG. 1 is a perspective view of the preferred embodiment of this invention.
Figure 2:
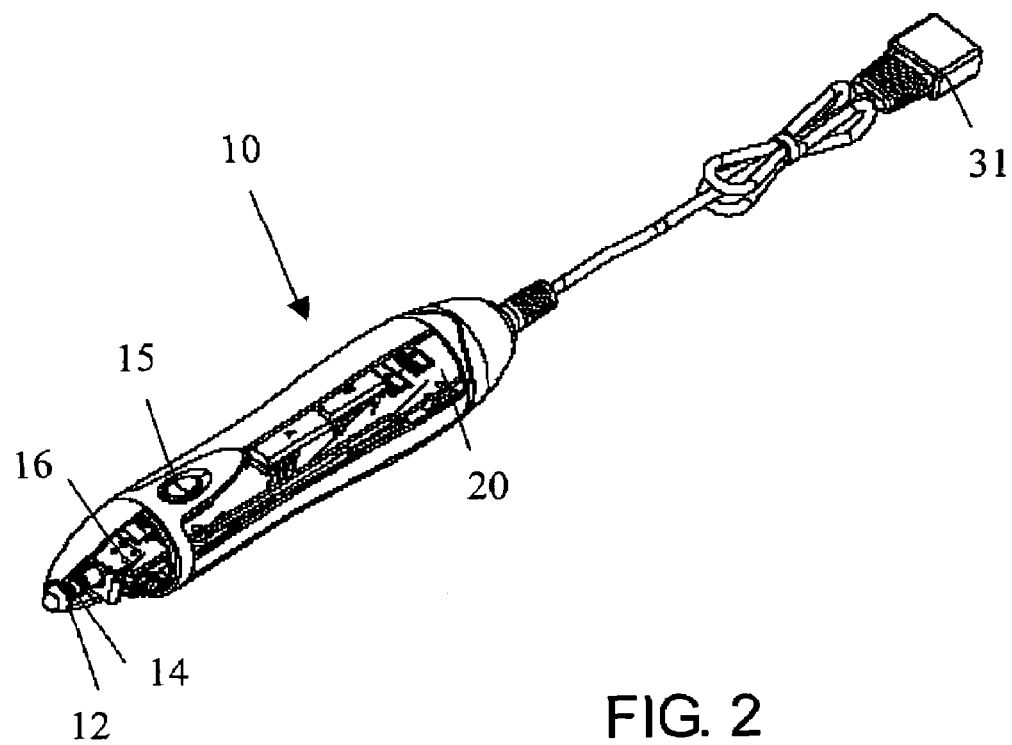
FIG. 2 is a partial sectional perspective view of FIG. 1.
Figure 3:
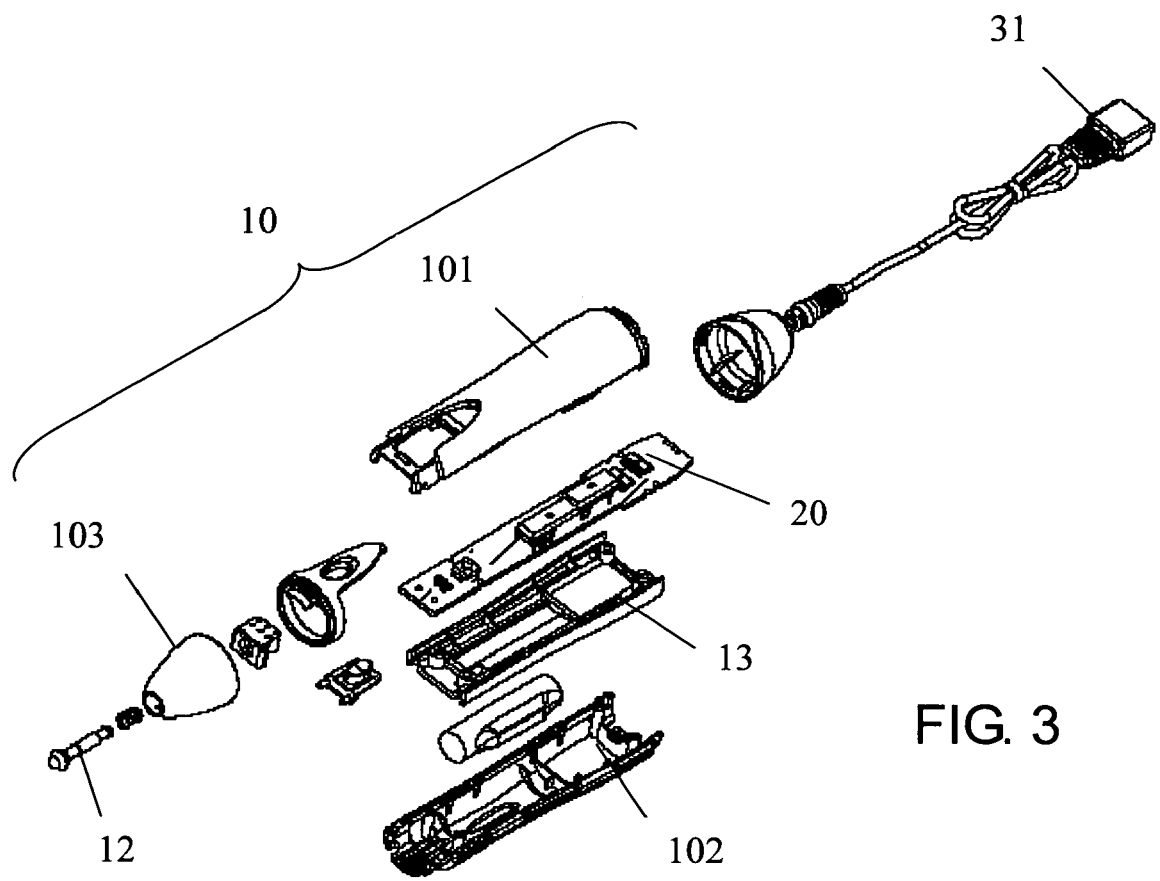
FIG. 3 is the exploded view of FIG. 1.
Figure 7:
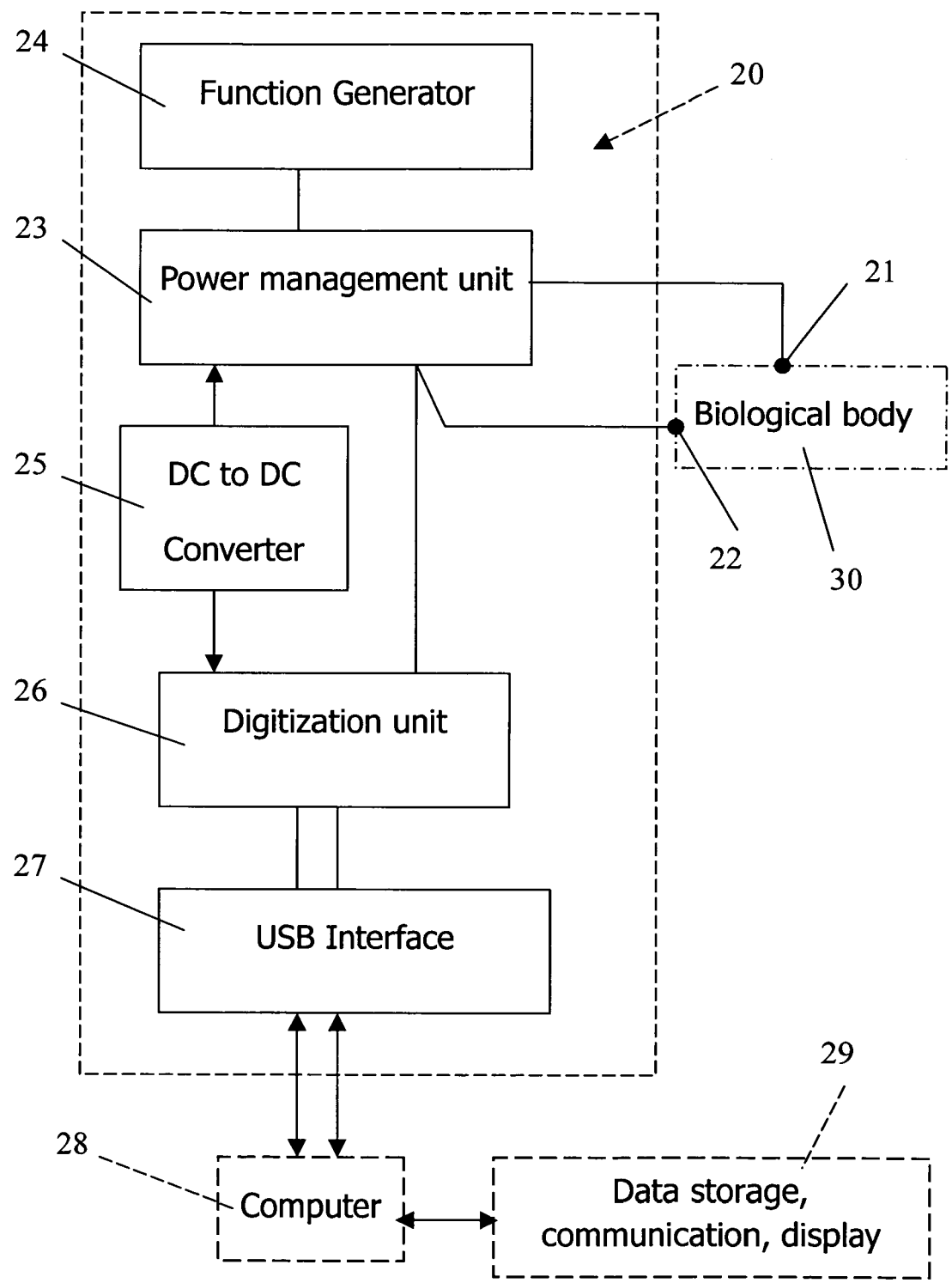
FIG. 7 is a block diagram of a preferred embodiment of this invention.

The preferred innovated impedance measuring device (10) with two electrical leads is shown as FIGS. 1 and 2. The probe (12) is used to contact the measuring area. The other electrical lead is located at hand held body (11) of the device. When electrical leads are contacted to the biological surface with the device activated, the impedance is measured and the data is sent to a personal computer for further processing. The process flow is shown in FIG. 7. The impedance measuring device (10) is pen like hand held instrument. The impedance measuring device (10) of this invention includes a hand held body (11), a probe (12) disposed at front portion of the impedance measuring device (10) and a USB connection (31). The hand held portion of main structure with hallow interior is composed of a top (101) and a bottom casing (102) holding the circuitry (20) of the device. The top and bottom of the hand held body (11) are joined together by the electrical conduction lead (13) that is connected to the impedance measuring circuitry (20) as shown in FIG. 3. As shown in FIG. 7, the electrical leads (21 and 22) of the circuitry are used for contacting to the biological surface. The impedance measuring circuitry (20) connected with two electrical leads (21 and 22), with the electrical leads (21) at the tip of probe (12) and the other electrical lead (22) is located on the outer surface of the cylinder of the hand held body (11). The electrical lead (22) is to a conduction element (13) of the hand held body (11), or is connected in parallel with extra hand held electrical lead (40) as shown in FIGS. 7 to 12.

As shown in FIG. 1 and FIG. 2, there is a control button (15) that can activate, interrupt the function of impedance measurement. A sound and/or lighting indicator are used to signal the completion of impedance acquisition. The control button (15) is also able to signal the data communication.

Figure 4:
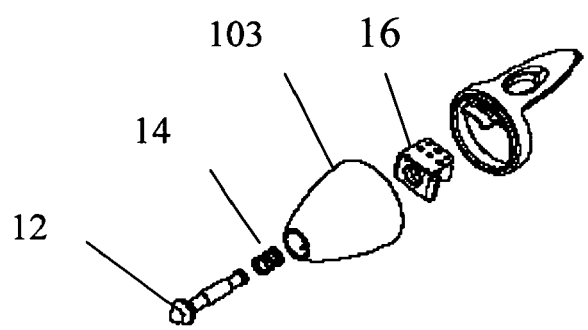
FIG. 4 is an enlarged view of the partial area in FIG. 3, showing the construction of the front-end portion of the probe.
Figure 6:
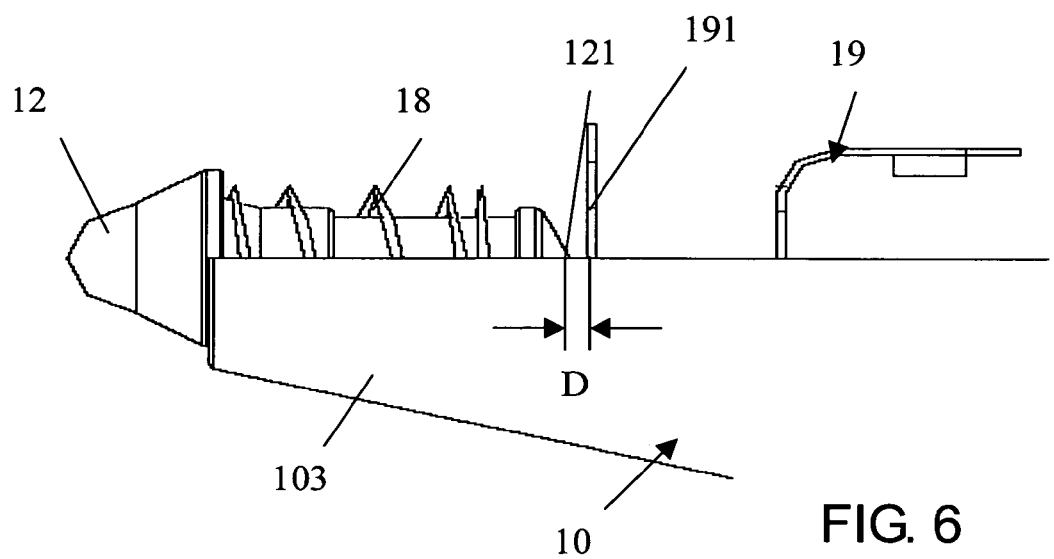
FIG. 6 is the partial sectional side view of FIG. 5.
Figure 5:
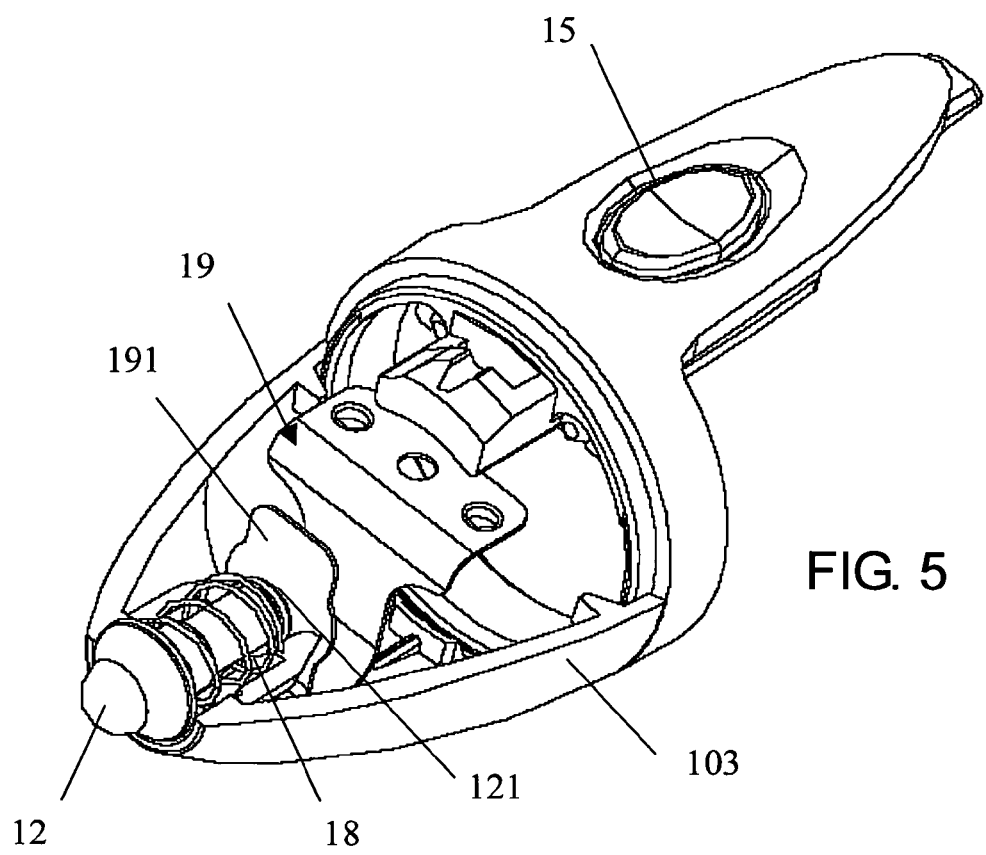
FIG. 5 is a partial sectional perspective interior view of front-end portion according to another preferred embodiment of this invention.

For applying a proper pressure to the biological body, the elastic unit is assembled with the probe (12) with minute spacer to absorb the pressure shock from impact. When measuring the biological impedance, the pressure is applied to connect the probe (12) to the circuitry. As shown in FIGS. 2, 3, and 4, the elastic unit, e.g., spring (14), and the supporting stopper (16) is assembled with probe (12) providing a minute sliding motion to absorb the applied pressure when measuring the impedance. The probe (12) and the elastic unit are situated in the front casing (103). The supporting stopper (16) is wired and connected to the measuring circuitry (20). When no pressure is applied to the probe (12), the probe (12) is virtually disconnected from the circuitry. Two views of elastic unit with its casing are shown in FIGS. 5 and 6.

The above pressure shock absorption design will hold the added stress and maintain unvarying contact, pressure and distant, to the measuring area. The same design will activate conduction of probe (12) to the circuitry when proper force is acted on the subject. As shown in FIGS. 5 and 6, the pressure shock absorption is composed from two elastic segments. The first segment is a spring unit (18) that supports the acted on pressure of the probe (12) and escort sliding back motion the probe (12) to the second elastic segment. The second elastic segment (19) is a U-shaped leaf spring (191). The one arm of U-shaped lead spring (191) is fixed on the circuitry. The other is a free arm of U-shaped leaf spring (191) that obvert to the measuring circuitry (20) and having a space D to back end (121) of the probe (12).

While the probe (12) is pressed against the surface of the object, the skin, the probe (12) is retracted and is acted onto the spring unit (18). If the retracted distance is greater that space D, the probe (12) will contact to the lead spring (19) and makes the conduction to the circuitry.

The measuring circuitry (20) includes a constant current source, shown as FIG. 7. The measuring circuitry (20) is composed of a function generator (24), e.g. a sine wave function generator, a signal condition and management unit (23) for providing powered functional signal to the measuring circuitry (20). The powered functional signal will be isolated and conditioned from the external source. The powered functional signal is conducted to the measuring area (21) through probe (12) and measuring area (22) through hand held conduction area (13) that will return and measure the impedance of measuring pressure point.

The power management unit (25) of the circuitry provides the isolated and sufficient current to the measuring circuitry (20), digitizer and USB communication at proper voltage levels. The measured data, and the impedance are transmitted, displayed, and stored into a computer for further processes processing. As shown in FIG. 1, the impedance measuring device utilizes a USB (27) connection and protocol with a connector (31) to communicate and interface with a personal computer (28) for data storage, communication, and display (29).

Figure 9:
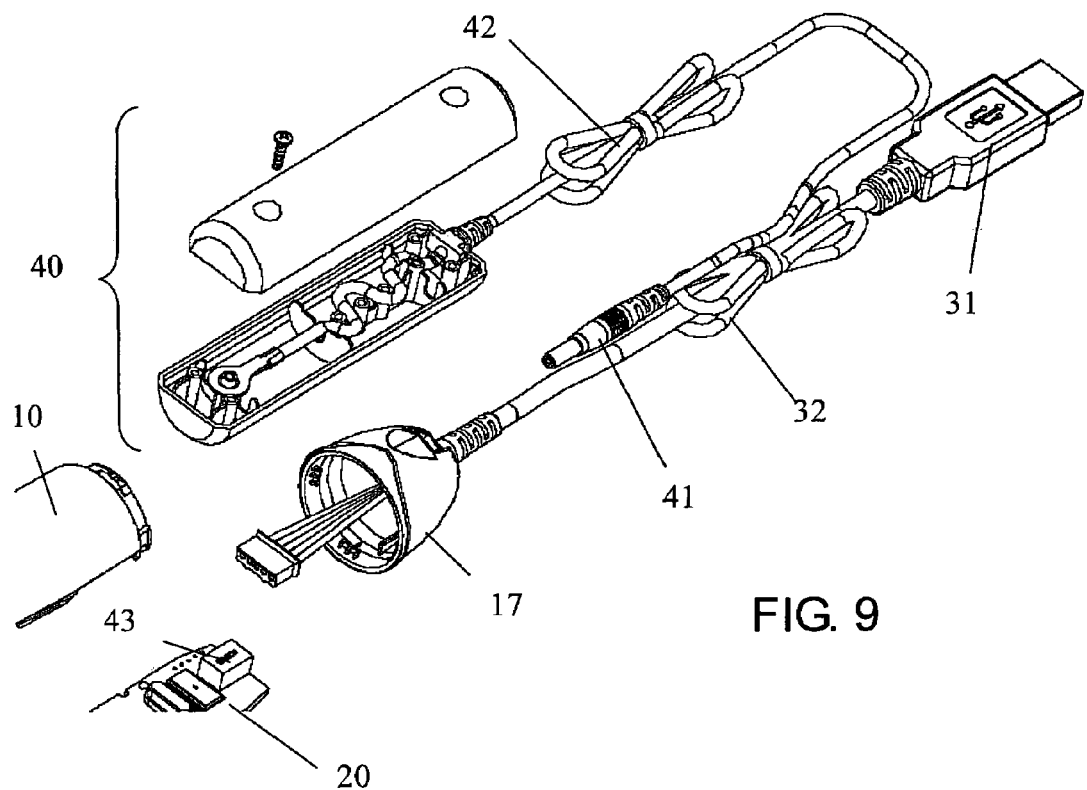
FIG. 9 is the partial exploded view of FIG. 8.
Figure 8:
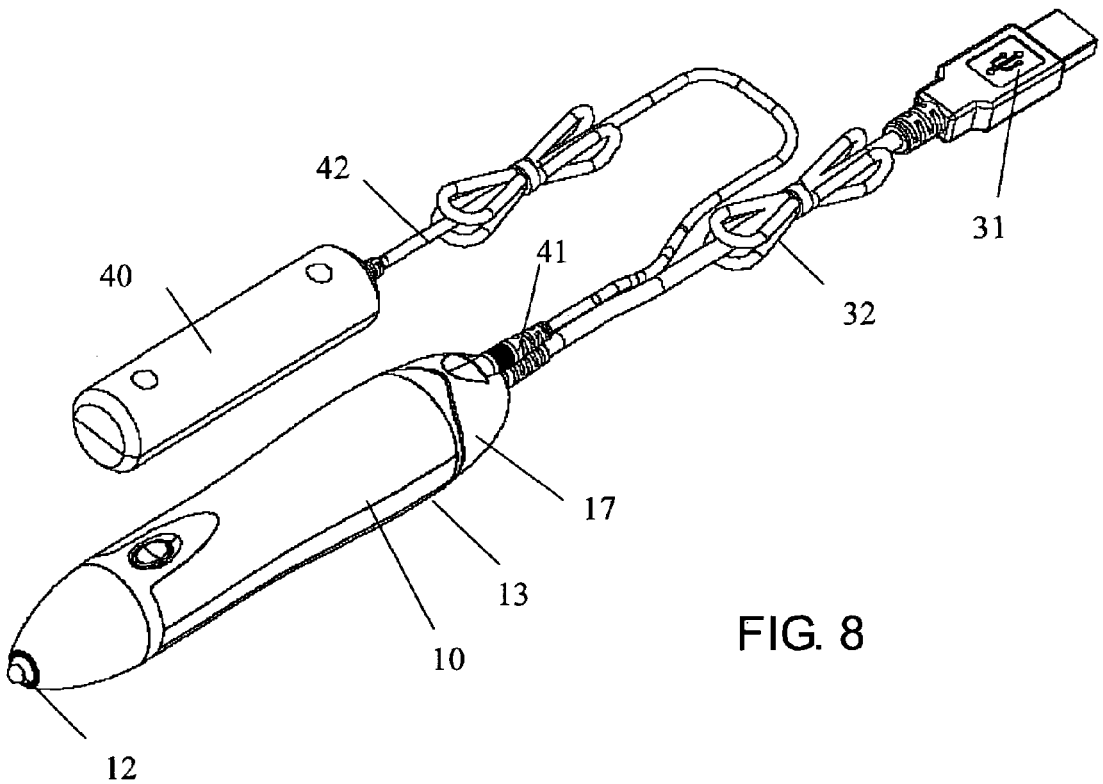
FIG. 8 is similar to the FIG. 1 showing another preferred embodiment with extra electrical lead of this invention.
Figure 11:
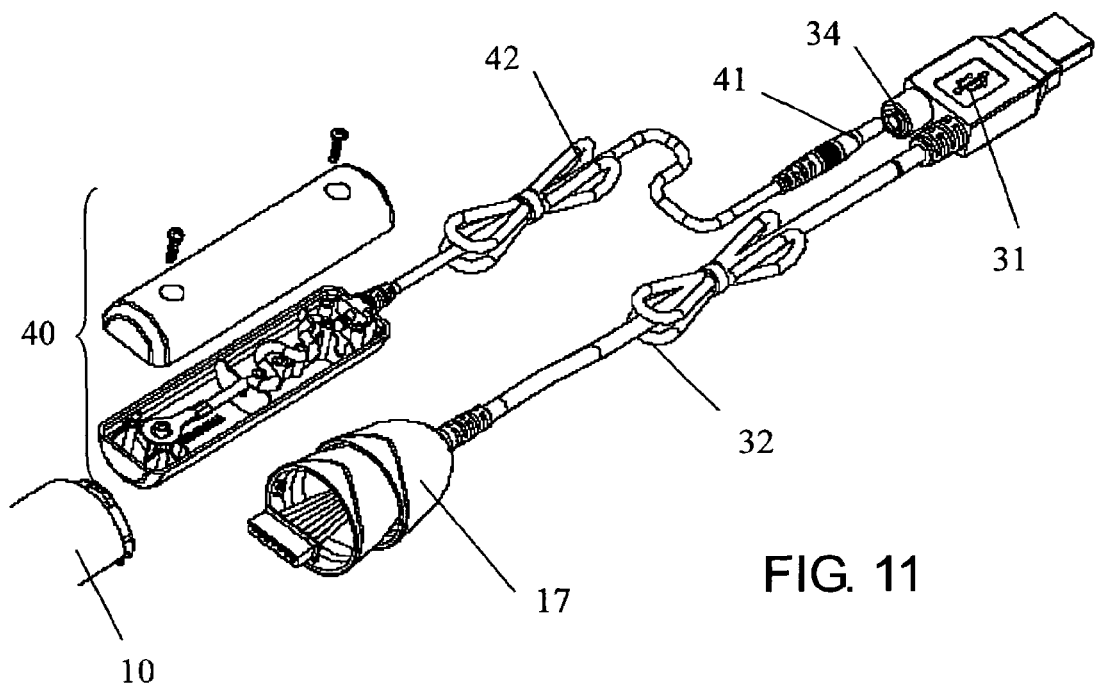
FIG. 11 is the partial exploded view of FIG. 10.
Figure 10:
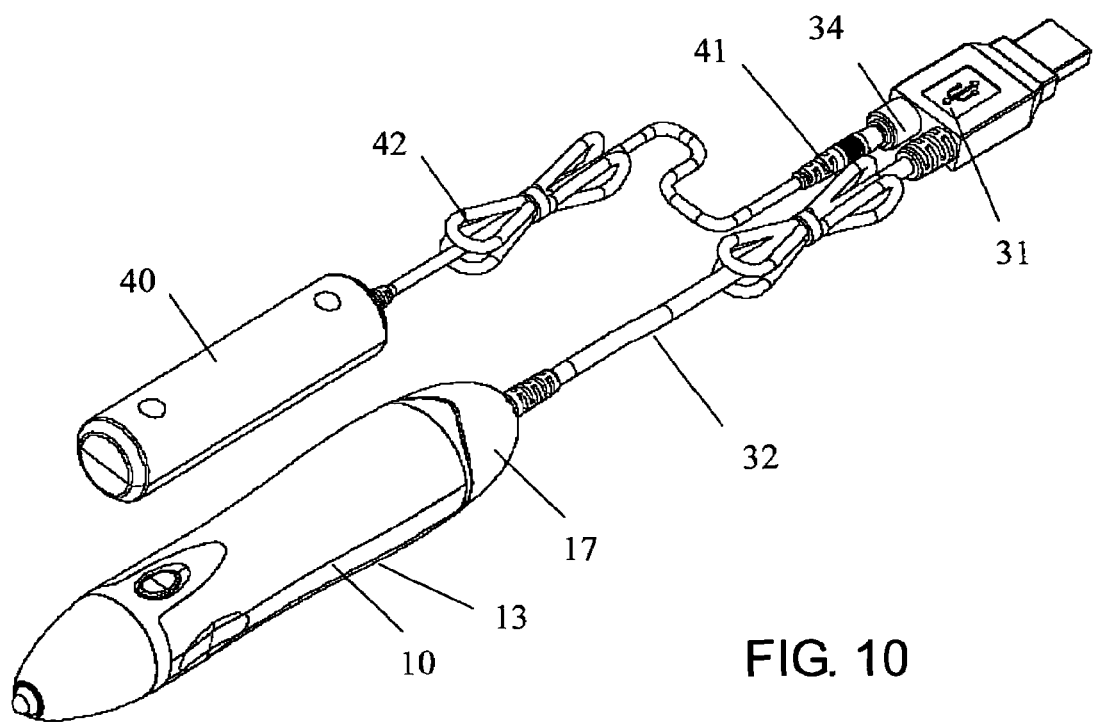
FIG. 10 is similar to the FIG. 8 showing another preferred embodiment of this invention.
Figure 12:
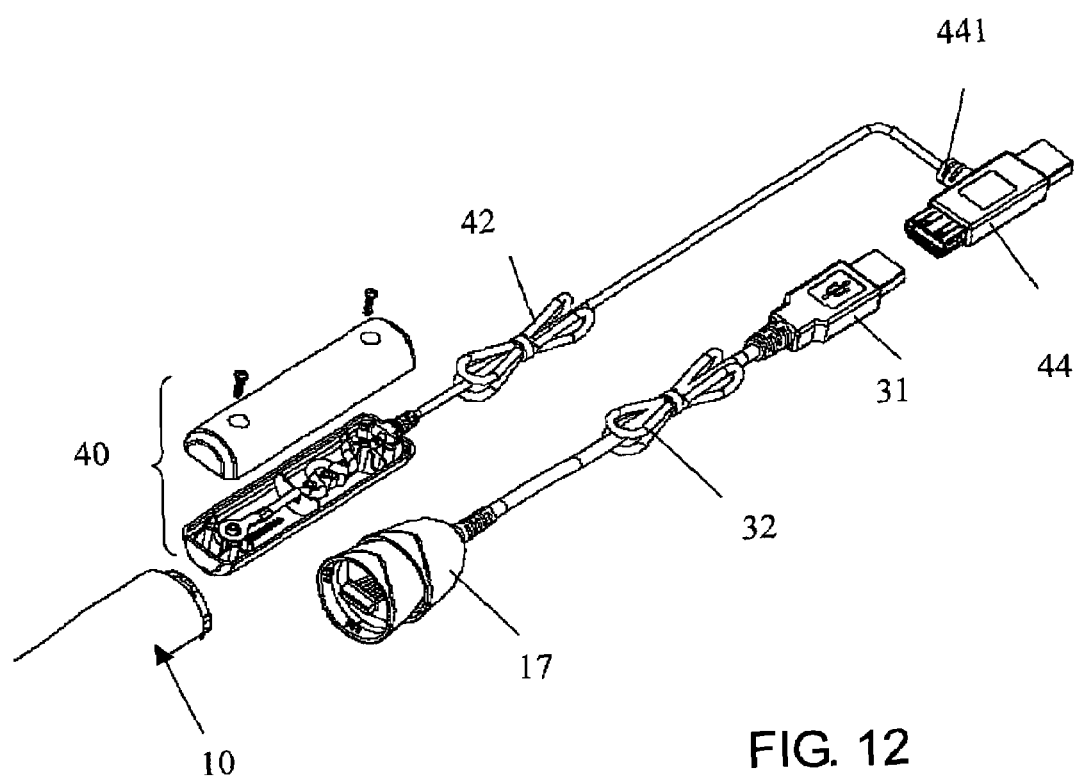
FIG. 12 is similar to the FIG. 8 showing another preferred embodiment with additional USB connector with electrical lead.

The above description illustrates a practical example of self-operated impedance measuring device (10). The impedance of pressure point can be measured by others using same circuitry as illustrated below. The configuration is shown as FIG. 8 and FIG. 9. The extra hand held electrical lead (40) has a connector (41) using extra electrical lead conduction wire (42) to the measuring device (10) through the tail end (17) of the impedance measuring device (10), as shown in FIG. 9. And the extra hand held electrical lead (40) is connected in parallel to the electrical lead of impedance measuring circuitry (20) through the receptacle (43) in the measuring device (10). The receptacle for the extra hand held electrical lead (40) can be at main body of the measuring device (10), at USB connector (31), or at USB extension connector (44). According to another embodiment of the present invention, a receptacle located at USB connector is shown in FIG. 10 and FIG. 1. The connector (41) of the extra hand held electrical lead is connected to the client end of USB connector. Furthermore, the structure of the receptacle of the extra hand held electrical lead located at the USB extension connector (44) is shown in FIG. 12. The connection of extra hand held electrical lead to the circuitry is through the side (441) of the USB extension connector (44). The present invention can be used by the clinical/medical practitioner to acquire impedance data from the subject. While the Extra hand held electrical lead (40) is used in the system, the electrical connection to the surface lead of main body of the measuring device is disconnected by the plug in of the extra hand held electrical lead to the receptacle. In this practice, the practitioner holds the main body of measuring device (10) and touches the subject with the probe (12), the current loop of impedance measuring circuitry (20) is through the subject holding the extra hand held electrical lead. Furthermore, the usage of current loop of impedance measuring device can be selected either from the computer or by the plug in of extra hand held electrical lead.

In summary, the impedance measuring device of the present invention has a specific design for self-operated impedance measurement as well as operated by practitioner. The impedance measuring device utilizes the USB connection and protocol to communicate and interface with a personal computer. The power from the computer is converted to the proper range and is isolated to the subject. The measured impedance data is stored into user database or can be used to consult with the remote server on the internet.

While the preferred embodiments of the methods have been described in reference to the environment in which they were developed, they are merely illustrative of the principles of this invention. Other embodiments and configurations may be devised without departing from the spirit of the inventions and the scope of the appended claims.

What is claimed:

1. A electrical impedance measuring device for homecare and e-Health environment acquiring electrical signal from a surface of a biological system, comprising: a measuring device with a hand held body and a probe located at a front tip of the hand held body, and two electrical conduction placements forming a electrical close loop; one of the electrical conduction placements being located at a front tip of the probe and the other electrical conduction placement being located at the hand held body; a first electric lead connected in parallel with a second electrical lead on an external surface of a cylinder of the hand held body; and a impedance measuring circuitry including a universal serial bus (USB) circuitry and communication protocol to interface with a personal computer, wherein the first electrical lead is connected in parallel with a universal serial bus (USB) connector.

2. The electrical impedance measuring device of claim 1, wherein the electrical impedance measuring device comprises a shape of a cylinder with a hollow interior that contains the impedance measuring circuitry.

3. The electrical impedance measuring device of claim 2, wherein the impedance measuring circuitry has a universal serial bus (USB) communication connection to interface with a computer.

4. The electrical impedance measuring device of claim 3, wherein the impedance measuring circuitry includes a universal serial bus (USB) personal computer communication protocol and circuitry interfacing to receive electrical power and to send and to receive digital data.

5. The electrical impedance measuring device of claim 1, wherein the probe is connected to an elastic unit to absorb a pressure when the probe impacts an object.

6. The electrical impedance measuring device of claim 5, wherein the elastic unit is composed of two segments; the probe can be pressed and retracted into the electrical impedance measuring device, and the probe comes in contact to the elastic unit.

7. The electrical impedance measuring device of claim 1, wherein wiring of the first electrical lead is connected in parallel with the universal serial bus (USB) connector that comes through from a tail end of hand held measuring body.

8. The electrical impedance measuring device of claim 2, wherein a control button located at the hand held body controls the impedance measuring circuitry that controls function of system activation, termination of system operation, activation of sound and light indicator when data acquiring procedure is completed, and commencement of data transmission.

9. The electrical impedance measuring device of claim 2, wherein the measuring circuitry comprises a function generator that provides a periodic electrical signal; and a power management unit and power isolation unit provide isolated current to the measuring circuitry when the electrical impedance measuring device is activated; and wherein a DC to DC converter provides isolated working power specification to the measuring circuitry; and an analog to digital converter converts the measured signal into digital format for uploading to a personal computer.

* * * * *